United States Patent [19]
Hafele

[11] Patent Number: 5,922,938
[45] Date of Patent: Jul. 13, 1999

[54] GAS SENSOR

[75] Inventor: Edelbert Hafele, Karlsruhe, Germany

[73] Assignee: Heraeus Electro-Nite International,N.V., Houthalen, Belgium

[21] Appl. No.: 08/732,472

[22] PCT Filed: May 5, 1995

[86] PCT No.: PCT/EP95/01713

§ 371 Date: Nov. 5, 1996

§ 102(e) Date: Nov. 5, 1996

[87] PCT Pub. No.: WO95/30893

PCT Pub. Date: Nov. 16, 1995

Related U.S. Application Data

[63] Continuation-in-part of application No. 08/234,991, filed as application No. PCT/EP93/00376, Feb. 16, 1993, Pat. No. 5,546,787.

[30] Foreign Application Priority Data

May 5, 1994 [DE] Germany ............................ 44 15 938

[51] Int. Cl.⁶ ............................ G01N 7/00; G01N 27/26
[52] U.S. Cl. ........................ 73/23.32; 73/31.05; 204/426
[58] Field of Search ................. 73/31.05, 23.2, 73/23.21, 23.32; 204/428, 426, 427

[56] References Cited

U.S. PATENT DOCUMENTS

| | | | |
|---|---|---|---|
| 4,214,472 | 7/1980 | Maxwell et al. | 73/23.2 |
| 4,320,378 | 3/1982 | Taniguchi et al. | 338/34 |
| 4,489,596 | 12/1984 | Linder et al. | 73/23.2 |
| 4,883,643 | 11/1989 | Nisshio et al. | 73/23.31 |
| 5,039,972 | 8/1991 | Kato et al. | 73/31.05 |
| 5,246,562 | 9/1993 | Weyl et al. | 204/424 |
| 5,467,636 | 11/1995 | Thompson et al. | 73/23.31 |
| 5,490,412 | 2/1996 | Duce et al. | 73/23.31 |
| 5,546,787 | 8/1996 | Häfele et al. | 73/23.31 |
| 5,602,325 | 2/1997 | McClanhan et al. | 73/23.31 |
| 5,616,825 | 4/1997 | Ache et al. | 73/23.31 |

*Primary Examiner*—Hezron Williams
*Assistant Examiner*—Jay L. Politzer
*Attorney, Agent, or Firm*—Antonelli, Terry, Stout & Kraus, LLP

[57] ABSTRACT

The invention relates to a gas sensor, preferably a lambda probe for determining pollutant and/or oxygen content in the exhaust of internal combustion engines or furnaces, with a metal housing that has mounting means for installing the gas sensor in an exhaust chamber, a ceramic part located inside the metal housing to receive a sensor support with sensor elements, one end of which projects into the exhaust chamber and whose other end is connectable with electrical terminals, characterized in that the ceramic part, in its area away from the exhaust, is secured by a positive connection in at least the radial direction in a metal housing and a sealing element is provided in an area of the ceramic part located downstream from the positive connection, said element being connected firstly with the outside wall of the ceramic part and secondly abutting a wall of the metal housing in a gas-tight manner.

16 Claims, 1 Drawing Sheet

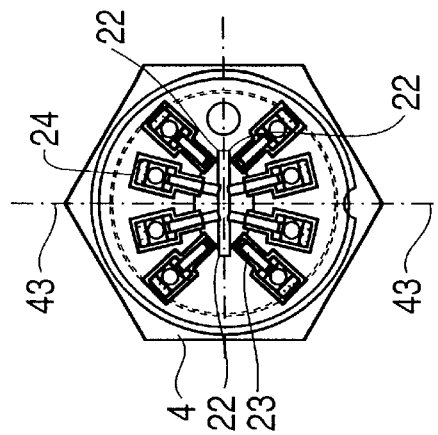
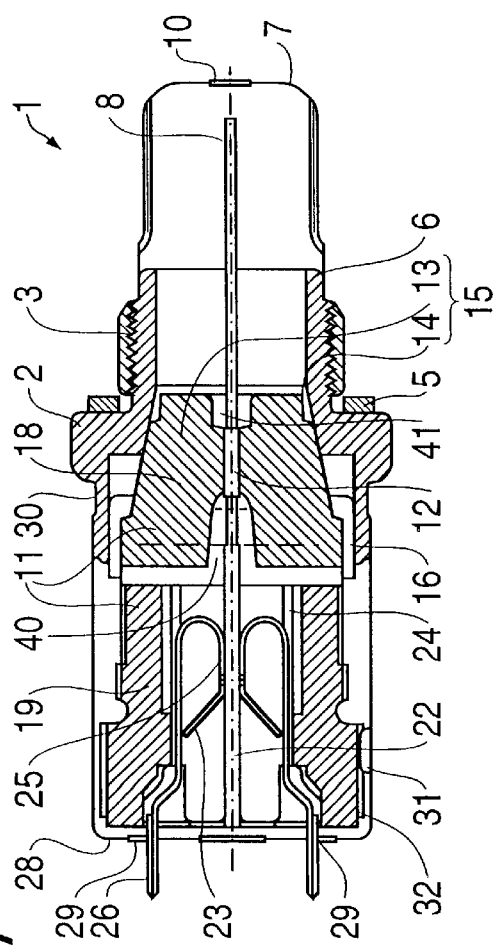

GAS SENSOR

This application is a continuation-in-part of U.S. patent application Ser. No. 234,991, filed Apr. 22, 1994, now U.S. Pat. No. 5,546,787, which is a 371 of International Application No. PCT/EP93/00376, filed Feb. 16, 1993.

The invention relates to a gas sensor, preferably a lambda sensor for determining the pollutant and/or oxygen content in exhaust according to the preamble of Claim 1.

Gas sensors according to the species are known (DE-42 04 850 A1) and have a ceramic part located in a protective housing to receive a sensor support that carries the sensor element itself at the end exposed to the exhaust, and whose other end projects into the contact area of contact elements. The contact elements contained in the ceramic part are in a conducting relationship with the electrical terminals projecting out of the protective housing.

For manufacturing reasons, the ceramic part is made of two pieces arranged mirror-image-fashion with respect to one another and having an identical shape, the shape of said pieces being designed so that, when the pieces are correctly positioned on top of one another, both the sensor support and the contact elements are fixed in position in the ceramic part.

Ceramic parts of this kind, because of the parting plane running in the lengthwise direction of the gas sensor, allow simple insertion and assembly of both the sensor support and the contact elements; however they have a relatively large parting plane. This imposes special requirements on the plane-parallelism of the two parting planes located opposite one another which, during the stoving process, for example during sintering of the two pieces, cannot always be met or can be met only with relatively high expense. If the two parting planes are not perfectly plane-parallel, sealing problems will occur.

The goal of the invention is to provide a gas sensor whose installation costs are minimized by ease of assembly of its individual parts.

This goal is achieved in a gas sensor according to the species by the characterizing features of the main claim.

As a result of the positive fit that prevails between the metal housing and the ceramic part, the latter is held in an extremely simple and secure fashion in the radial direction in the metal housing, and the gas-sealing surfaces provide a seal for the gas escaping from the exhaust chamber. If this positive fit is designed as a tapered connection and the taper ratio is chosen accordingly, an axial locking of the ceramic part is achieved, so that an additional sealing element possibly located between the ceramic part and the metal housing is exposed only to a pressure that is considerably reduced by comparison to the pressure prevailing in the exhaust chamber.

Further advantageous embodiments and improvements as well as advantages follow from the subclaims.

The invention will now be described in greater detail with reference to a preferred embodiment shown in the drawings.

FIG. 1 is a lengthwise section through the gas sensor according to the invention;

FIG. 2 is a top view of FIG. 1, partially cut away; and

FIG. 3 is a side view of the gas sensor.

The gas sensor designated as a whole by 1 in FIG. 1 has a metal housing 2 provided with a screw thread 3 at its end facing the exhaust. An Allen wrench 4 is associated with screw thread 3, with the aid of which wrench gas sensor 1 can be screwed into a matching thread of an exhaust chamber, not shown, with a sealing ring 5 in between.

At its forward end, metal housing 2 has a cylindrical projection 6 that serves to receive a protective sheath 7 for a sensor support 8 with sensor elements 9 located on it and printed for example. Protective sheath 7 is provided in a manner known of itself with feedthroughs 10 so that the exhaust can flow around sensor element 9.

A ceramic part 11 serves to receive sensor support 8, said part having a feedthrough slot 12 for the sensor support and projecting into the exhaust chamber, not shown, with its (at least) one sensor element mounted thereon. For a gas-tight seal of feedthrough 12 in its area facing the exhaust, the feedthrough can be potted or sensor support 8 can be glued in feedthrough 12. Two recesses 40, 41 are also provided for this purpose, with a temperature-resistant and less gas-tight sealing material, ceramic adhesive for example, being added to recess 41 on the exhaust side and a less temperature-resistant but more gas-tight sealing material being added to the other recess 40.

Area 13 of ceramic part 11 on the exhaust side is made frustoconical around feedthrough slot 12 and projects into a matching conical first bore 14 of metal housing 2. Ceramic part 11 is fixed in position by the positive connection 15 thus formed in the radial direction in metal housing 2. With a suitable design for the taper ratio, ceramic part 11 can also be fixed in the axial direction inside metal housing 2. In order to be able to manufacture the two cones with relatively large tolerances, ceramic part 11 can be secured in position within the metal housing by an additional glued connection.

As can be seen from FIG. 2, an essentially annular sealing element 16 is fastened on the outside wall of frustoconical area 13 on the exhaust side of ceramic part 11, said element 16, in a preferred embodiment of the gas sensor, abutting the wall of a second bore 17 provided in metal housing 2 flexibly with pretensioning, thus preventing escape of the exhaust. Ceramic part 11 is connected by high-temperature soldering with sealing element 16 which in turn is welded in an exhaust-tight manner in second bore 17. The pretensioning can be achieved either by sealing element 16 or by a spring washer in the area facing away from the exhaust.

Ceramic part 11 in the embodiment shown is formed by two pieces 18, 19 arranged axially with respect to one another, with one piece 18 being located essentially within metal housing 2 and fixed in position in the latter in the manner described above, and sensor support 8 projects by a certain amount out of one piece 18.

One piece 18, at its end facing the other piece 19, has at least one projection 20 that projects into a recess 21 provided in the end of the other piece 19. The other piece 19 is provided with a receiving slot 22 that corresponds to feedthrough slot 12 in a piece 18, said slot serving to receive the area of sensor support that projects opposite piece 18.

The other piece 19 also serves to receive contact elements 23 located within eight incorporated slots 24. Slots 24 (see FIG. 3) are directed radially and each extend as far as receiving slot 22, with respect to which, and with respect to its perpendicular central plane, they are arranged with mirror symmetry. The further they are located from vertical central plane 43, the more they differ from a rectangular alignment relative to slot 22.

Contact elements 23 are made U-shaped at one end, so that they, with their area 25 running primarily parallel to sensor support 8, abut the latter flexibly and connect the electrical traces provided on sensor support 8, not shown, for example printed or vapor-deposited traces, and thus connect sensor element 9 with electrical terminals 26.

To encapsulate gas sensor 1, a sheath 27 is provided whose bottom 28 has openings 29 traversed by electrical connections 26. The other end of sheath 27 is permanently connected with a cylindrical projection 30 of the metal housing. In the vicinity of the bottom, sheath 27 has an inwardly directed projection 31 that engages one of two grooves 32 provided in piece 19 in order thus to establish the relative position of terminals 26 with respect to openings 29 provided in bottom 28.

I claim:

1. Gas sensor, preferably a lambda probe for determining the pollutant and/or oxygen content of exhaust from internal combustion engines or furnaces, with a metal housing that has mounting means for installing the gas sensor in an exhaust chamber, a ceramic part located inside the metal housing to receive a sensor support with at least one sensor element that projects into the exhaust chamber with the end of the sensor support at the exhaust end, and whose other end is connectable with electrical terminals, characterized in that ceramic part (11) is fastened in a gas-tight manner in its area on the exhaust side by means of a positive connection (15) forming a gas-sealing surface in at least the radial direction in metal housing (2).

2. Gas sensor according to claim 1, characterized in that a sealing device (16) is provided in an area of ceramic part (11) located beyond the positive connection, said sealing device abutting in a gas-tight manner the outside wall of ceramic part (11) on one side and an internal wall of metal housing (2) on the other side.

3. Gas sensor according to claim 2, characterized in that sealing device (16) is designed as a sealing element (16) connected with the outside wall of ceramic part (11).

4. Gas sensor according to claim 1, characterized in that ceramic part (11) is held in place by the positive connection (15) in the metal housing in an axial direction.

5. Gas sensor according to claim 1, characterized in that ceramic part (11) for forming the gas-sealing surfaces of positive connection (15) is made frustoconical in its area (13) on the exhaust side, and metal housing (2) has a suitably tapered first bore (14).

6. Gas sensor according to claim 1, characterized in that one end of a sealing element (16) is permanently connected with the outside wall of frustoconical area (13) of ceramic part (11) and the area of the other end, with pretensioning, abuts one wall of a second bore (17) provided in the metal housing (2).

7. Gas sensor according to claim 6, characterized in that the end of sealing element (16) is connected in a gas-tight manner with the metal housing (2).

8. Gas sensor according to claim 1, characterized in that ceramic part (11) is subdivided in the axial direction into two pieces (18, 19) located inside metal housing (2), one of which pieces (18) is permanently connected with sensor support (8) and the other (19) receives contact elements (23) and has a receiving slot (22) for sensor support (8).

9. Gas sensor according to claim 8, characterized in that one of pieces (18) has a projection (20) at its end that faces the other piece (19), said projection projecting into a recess (21) provided in the other piece (19).

10. Gas sensor according to claim 1, characterized in that ceramic part (11), at an outer circumferential jacket surface at an end opposite the exhaust side, has a groove (32) essentially aligned parallel to a lengthwise axis of the ceramic part and receiving a projection (31) provided on a sheath (27) surrounding ceramic part (11).

11. Gas sensor according to claim 10, characterized in that the groove (32) is located in the vicinity of the end of ceramic part (11) away from the exhaust.

12. Gas sensor according to claim 8, characterized in that one piece (18) of ceramic part (11) in the area of a feedthrough slot (12) through which the at least one sensor element projects, has a recess (41) on the exhaust side and a recess (40) away from the exhaust side to receive sealing material.

13. Gas sensor according to claim 8, characterized in that contact elements (23) are located in slots (24).

14. Gas sensor according to claim 13, characterized in that the slots (24) are arranged with mirror symmetry with respect to the receiving slot (22).

15. Gas sensor according to claim 14, characterized in that the slots (24) are arranged with mirror symmetry with respect to rectangular central plane (43) of the receiving slot (22).

16. Gas sensor according to claim 14, characterized in that the slots (24), with respect to the receiving slot (22), deviate increasingly from its rectangular extent with increasing distance from rectangular central plane (43).

* * * * *